(12) United States Patent
Jang et al.

(10) Patent No.: US 11,209,445 B2
(45) Date of Patent: Dec. 28, 2021

(54) BLOOD TESTING APPARATUS AND CONTROL METHOD THEREOF

(71) Applicant: SAMSUNG ELECTRONICS CO., LTD., Suwon-si (KR)

(72) Inventors: Eun Jeong Jang, Suwon-si (KR); Ki Ju Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 163 days.

(21) Appl. No.: 16/276,077

(22) Filed: Feb. 14, 2019

(65) Prior Publication Data

US 2019/0250174 A1    Aug. 15, 2019

(30) Foreign Application Priority Data

Feb. 14, 2018  (KR) .................. 10-2018-0018655
Aug. 31, 2018  (KR) .................. 10-2018-0103975

(51) Int. Cl.
| | | |
|---|---|---|
| *B01L 3/00* | (2006.01) | |
| *G01N 33/80* | (2006.01) | |
| *G01N 35/00* | (2006.01) | |
| *G01N 33/50* | (2006.01) | |
| *B01L 9/00* | (2006.01) | |

(52) U.S. Cl.
CPC ............ *G01N 33/80* (2013.01); *B01L 3/508* (2013.01); *B01L 9/52* (2013.01); *G01N 33/5005* (2013.01); *G01N 35/00732* (2013.01); *B01L 2200/143* (2013.01); *B01L 2300/025* (2013.01); *G01N 2035/00752* (2013.01); *G01N 2035/00772* (2013.01); *G01N 2035/00831* (2013.01); *G01N 2035/00891* (2013.01)

(58) Field of Classification Search
CPC ........ G01N 33/80; G01N 33/50; G01N 33/48; B01L 3/508; B01L 3/50; B01L 9/52; B01L 9/00; G06F 19/36
USPC ................ 422/50, 68.1; 436/43; 702/19, 22
See application file for complete search history.

(56) References Cited

U.S. PATENT DOCUMENTS

| | | | |
|---|---|---|---|
| 6,391,263 B1 * | 5/2002 | Mishima | G01N 35/00732 422/67 |
| 8,958,990 B2 * | 2/2015 | Hirayama | G16H 40/67 702/19 |
| 2005/0019943 A1 | 1/2005 | Chaoui et al. | |
| 2006/0004530 A1 * | 1/2006 | Miyamoto | G01N 15/1459 702/30 |
| 2009/0006003 A1 | 1/2009 | Hirayama et al. | |

(Continued)

OTHER PUBLICATIONS

Written Opinion (PCT/ISA/237) issued by the International Searching Authority in corresponding International Application No. PCT/KR2019/001788, dated Jun. 12, 2019.

(Continued)

*Primary Examiner* — Christine T Mui
(74) *Attorney, Agent, or Firm* — Sughrue Mion, PLLC

(57) ABSTRACT

A blood testing apparatus includes an analyzer configured to analyze blood components of an animal that are included in a test medium; an output device configured to display analysis results of the blood components; and a controller configured to determine a species of the animal based on at least one from among types of the blood components and the analysis results of the blood components and control the output device to display the determined species of the animal.

13 Claims, 25 Drawing Sheets

(56) References Cited

U.S. PATENT DOCUMENTS

2010/0248349 A1    9/2010    Nakamura et al.
2012/0072126 A1    3/2012    Yoshida et al.
2012/0124387 A1    5/2012    Skocic

OTHER PUBLICATIONS

International Search Report (PCT/ISA/210), issued by International Searching Authority in corresponding International Application No. PCT/KR2019/001788, dated Jun. 12, 2019.

* cited by examiner

FIG. 8A

| Back | Analysis Information |
|---|---|

| Patient ID | Patient_1234 |
| Client ID | Hong |
| Species | Feline ... | Sample | Serum ▼ |
| Gender | Neutered ... | Age | Yrs ▼ |

| Back | Patient_1234 | | | |
|---|---|---|---|---|
| Cartridge:AABBCC | | | | Species:Feline |
| Analyte | Result | Ref.Range | Unit | ▲ |
| ALT | ① 0.1 | 8~40 | Mmol/L | 1/7 |
| AST | 38.7 | 5~34 | mEq/L | |
| GGT | 20.1 | 11~63 | Ukat/L | ▼ |

Print | Complete

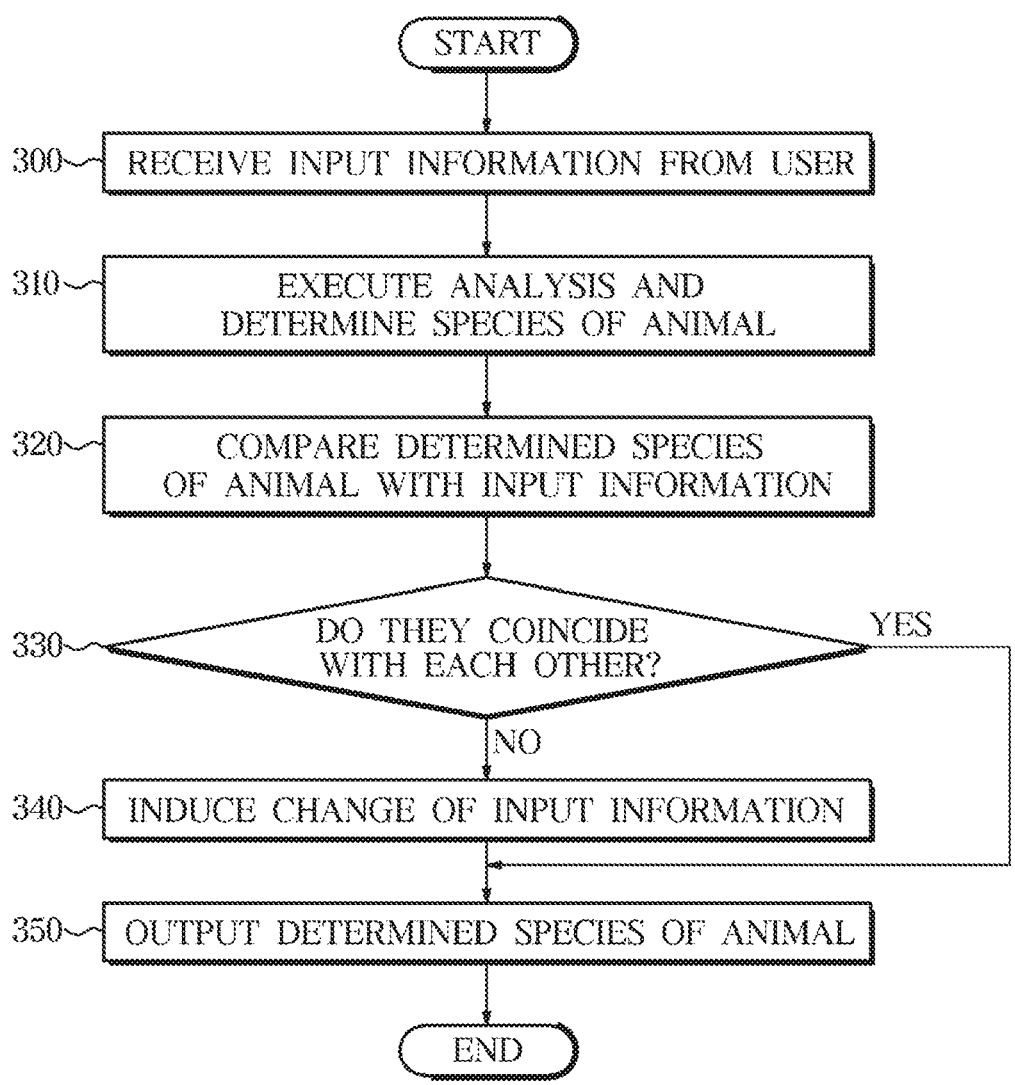

FIG. 10

Pet Information

PET ID*
[12345678]

PET NAME*
[DDD]

BREED SIZE
[DEA1.1]

SEX*
[Male]

COMMENTS
[          ]

SPECIES
[Feline]

AGE
[7]

WEIGHT
[4.5kg]

HEIGHT
[25cm]

DO YOU WANT TO EXECUTE TEST?
[YES]  [NO]  [CHANGE]

1000

Exam Result.

| CARTRIDGE A | |
|---|---|
| BLOOD COMPONENT | ANALYSIS RESULT |
| ALB | 5 |
| ALP | 100 |
| ALT | 200 |
| ... | ... |
| CREA | 7 |

DETERMINED SPECIES OF ANIMAL
[CANINE]

DO YOU WANT TO CHANGE SPECIES?
[YES]  [NO]

Back | Analysis Information — 1010

Patient ID: Patient_1234
Client ID: Hong
Species: Feline   Sample: Serum
Gender: Neutered   Age: __ Yrs

OK

⇩

Patient_1234

Client ID : Hong
Species : Feline
Sample : Serum
Gender : Neutered
Cartridge : AABBCC Time Remaining
04:30

Cancel

⇩

Back | Patient_1234

Cartridge:AABBCC                Species:Feline

| Analyte | Result | Ref.Range | Unit |
|---------|--------|-----------|------|
| ALT | 0.1 | 8-40 | Mmol/L |
| AST | 38.7 | 5-34 | mEq/L |
| GGT | 20.1 | 11-63 | Ukat/L |

1/7

Print | Complete | Change Species — 1018

FIG. 13B

| Back | Choose Species | |
|---|---|---|
| Main | Other(a~h) | Other(i~z) |
| | Canine | |
| | Equine | |
| | Feline | |
| | Bovine | |
| | Avian | |

Change

⬇

Back  Patient_1234

Cartridge:AABBCC                    Species:Canine

| Analyte | Result | Ref.Range | Unit |
|---|---|---|---|
| ALT | ① 0.7 | 8~40 | Mmol/L |
| AST | ① 35 | 5~30 | mEq/L |
| GGT | 20.1 | 10~80 | Ukat/L |

1/7

Print    Complete    Change Species

~1020

~1022

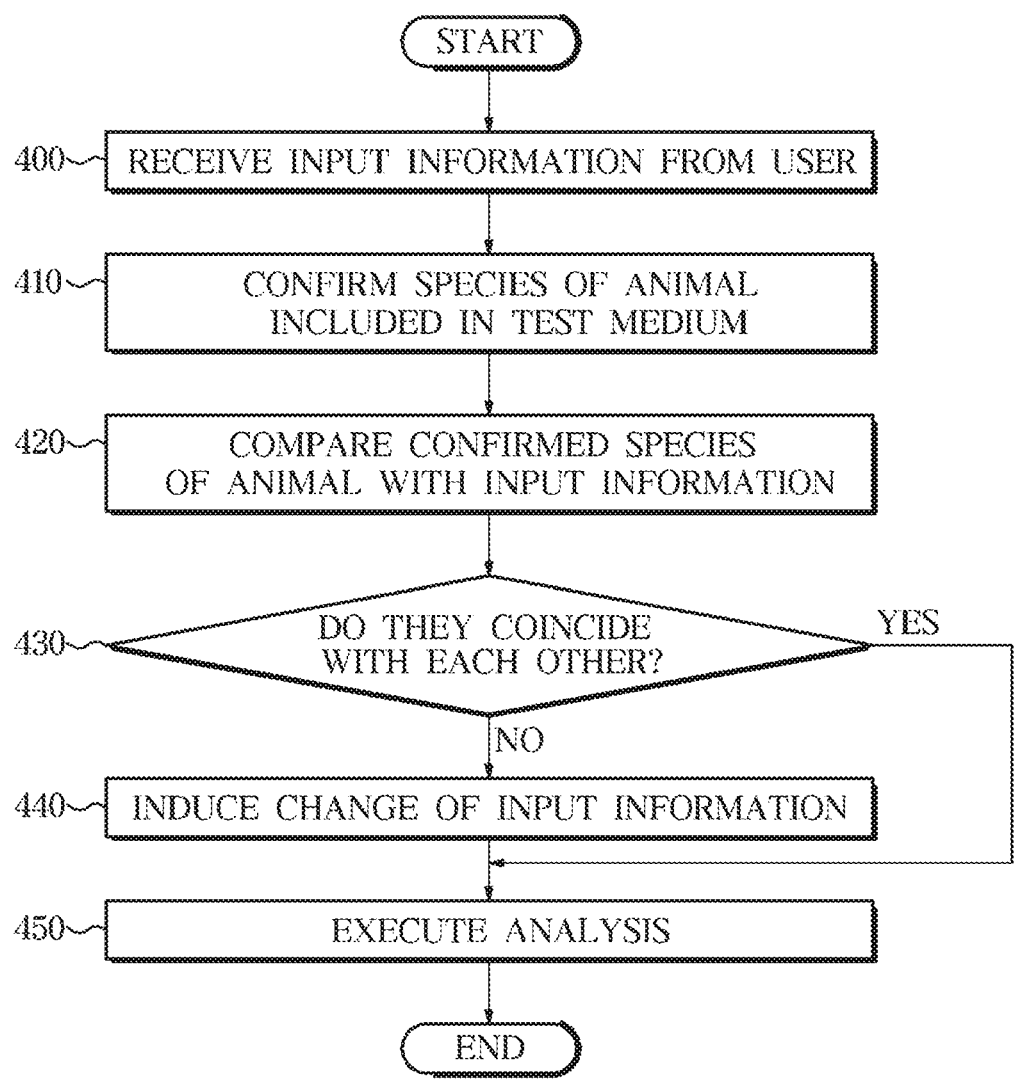

FIG. 15B

Choose Species screen (1510): Main | Other(a~h) | Other(i~z) tabs; list: Canine, Equine, Feline, Bovine, Avian; 1/2; Change button; Back.

Patient_1234 (1512):
- Client ID : Hong
- Species : Canine
- Sample : Serum
- Gender : Neutered
- Cartridge : AABBCC Time Remaining 04:30; Cancel.

Patient_1234 results (1514): Cartridge:AABBCC  Species:Canine

| Analyte | Result | Ref.Range | Unit |
|---|---|---|---|
| ALT | ① 0.7 | 8~40 | Mmol/L |
| AST | ① 35 | 5~30 | mEq/L |
| GGT | 20.1 | 10~80 | Ukat/L |

1/7; Print | Complete | Change Species; Back.

| Back | Choose Species | |
|---|---|---|
| Main | Other(a~h) | Other(i~z) |
| | Canine | |
| | Equine | |
| | Feline | 1/2 |
| | Bovine | |
| | Avian | |

Change

~1510

~2010

| Back | Patient_1234 | | | |
|---|---|---|---|---|
| Cartridge:AABBCC | | | | Species:Canine |
| | Analyte | Result | Ref.Range | Unit |
| | ALT | ① 0.7 | 8~40 | Mmol/L |
| | AST | ① 35 | 5~30 | mEq/L |
| | GGT | 20.1 | 10~80 | Ukat/L |

Print | Complete | Change Species

~1514

BLOOD TESTING APPARATUS AND CONTROL METHOD THEREOF

CROSS-REFERENCE TO RELATED APPLICATION(S)

This application is based on and claims priority under 35 U.S.C. § 119(a) to Korean Patent Applications Nos. 10-2018-0018655 and 10-2018-0103975, filed on Feb. 14, 2018 and Aug. 31, 2018, respectively, in the Korean Intellectual Property Office, the disclosures of which are incorporated by reference herein in their entireties.

BACKGROUND

1. Field

The disclosure relates to a blood testing apparatus which determines a species of an animal and outputs the determined species to a user, and a control method thereof.

2. Description of Related Art

In animal hospitals, a veterinarian executes various tests using clinical pathology examination equipment to determine a disease of an animal and, as one example thereof, a blood testing apparatus is used.

The blood testing apparatus is an apparatus used to determine a current health condition of an animal by analyzing a small amount of blood taken from the animal, and may easily acquire information about the animal through a comparatively simple method, such as blood collection, and, thus, is widely used.

Unlike humans, there are various animal species and, in order to execute a blood test on an animal, the blood test should be executed under the condition that animal species and characteristics thereof are accurately recognized. For example, when cat is input to a blood testing apparatus as an animal species but the actual sampled blood is blood of a dog, an error in determination according to results of the blood test may occur due to the differences in normal ranges between the respective species.

However, the related art blood testing apparatus only displays information input by a user, and does not determine a species of an animal through test results and thereby cannot indicate that a user input indicating the species is incorrect.

SUMMARY

Provided is a blood testing apparatus which predicts a species of an animal using analysis results and, when the predicted species of the animal differs from a species of the animal chosen by a user prior to a test, gives a warning to the user through various interfaces to prevent misdiagnosis according to incorrect choice of the species of the animal and a control method thereof.

Additional aspects will be set forth in part in the description which follows and, in part, will be apparent from the description, or may be learned by practice of the presented embodiments.

In accordance with an aspect of the disclosure, a blood testing apparatus includes an analyzer configured to analyze blood components of an animal included in a test medium on the basis of the blood components, an output device configured to display analysis results of the blood components and a species of the animal, and a controller configured to determine the species of the animal based on at least one of types of the blood components and the analysis results of the blood components and control the output device to display the determined species of the animal.

The blood testing apparatus may further include an input device configured to receive an input command from a user, and the controller may compare the determined species of the animal with a species of the animal included in input information input by the user and output an interface configured to prompt the user to change the input information based on a comparison result.

The controller may confirm the species of the animal whose blood components are in the test medium, compare the confirmed species of the animal with the species of the animal included in the input information, and control the analyzer based on a comparison result.

The controller may confirm the species of the animal through at least one of a barcode, a Quick Response (QR) code, a radio frequency identification (RFID) tag, and a universal serial bus (USB) chip included in the test medium.

The controller may control the output device to display an interface configured to prompt the user to change the input information based on the comparison result.

The controller may extract raw data of the blood components through the analyzer, execute a first analysis based on the raw data and the species of the animal included in the input information input by the user, and determine the species of the animal based on analysis results of the first analysis.

The controller may execute a second analysis based on the raw data and the changed input information, and display analysis results of the second analysis through the output device.

The controller may determine the species of the animal based on a learning model obtained through machine learning for the types of the blood components and the analysis results of the blood components.

The controller may update the learning model by calculating first output values of activation functions based on weights set according to the types of the blood components and the analysis results of the blood components, and by varying the weights based on differences between the first output values and the species of the animal included in the input information input by the user.

In accordance with an aspect of the disclosure, a blood testing apparatus includes an input device configured to receive input information from a user, an analyzer configured to analyze blood components of an animal included in a test medium, an output device configured to display the input information and analysis results of the analyzer, and a controller configured to confirm a species of the animal by reading the test medium, compare the confirmed species of the animal with a species of the animal included in the input information, and control the output device to output an interface configured to prompt the user to change the input information based on a comparison result.

The controller may confirm the species of the animal through at least one of a barcode, a QR code, an RFID tag, and a USB chip included in the test medium.

The controller may control the analyzer to analyze the blood components, when the confirmed species of the animal coincides with the species of the animal included in the input information.

In accordance with an aspect of the disclosure, a control method of a blood testing apparatus includes analyzing blood components of an animal included in a test medium on the basis of the blood components, determining a species of the animal based on at least one of types of the blood components and analysis results of the blood components, and displaying the analysis results of the blood components and the determined species of the animal.

The control method may further include receiving an input command from a user, and the receiving of the input command from the user may include comparing the determined species of the animal with a species of the animal included in input information input by the user, and the displaying of the analysis results of the blood components and the determined species of the animal may include displaying an interface configured to prompt the user to change the input information based on a comparison result.

The control method may further include confirming the species of the animal whose blood components are in the test medium prior to analyzing the blood components and displaying a result of comparison between the confirmed species and the species of the animal included in the input information.

The determining of the species of the animal may include extracting raw data of the blood components, executing a first analysis based on the species of the animal included in the input information input by the user, and determining the species of the animal based on analysis results of the first analysis.

The displaying may include executing a second analysis based on the raw data and the changed input information and displaying analysis results of the second analysis.

The determining of the species of the animal may include determining the species of the animal based on whether or not the analysis results of the blood components are predetermined reference values or more.

The determining of the species of the animal may include determining the species of the animal based on blood components extracted from a first test medium and blood components extracted from a second test medium, types of which are different from those of the blood components extracted from the first test medium.

BRIEF DESCRIPTION OF THE DRAWINGS

The above and other aspects, features, and advantages of certain embodiments of the present disclosure will be more apparent from the following description, taken in conjunction with the accompanying drawings, in which:

FIGS. 8A, 8B, and 8C are views of exemplary interfaces illustrating problems of a related art blood testing apparatus;

FIG. 9 is a flowchart illustrating a method of inducing change of an input species of an animal according to an embodiment;

FIG. 10 is a view exemplarily illustrating interfaces configured to induce change of a species according to an embodiment;

FIGS. 13A and 13B are views exemplarily illustrating interfaces according to an embodiment;

FIG. 14 is a flowchart illustrating a method of inducing change of a species of an animal according to an embodiment;

FIGS. 15A and 15B are views exemplarily illustrating interfaces according to an embodiment;

FIGS. 20A and 20B are views exemplarily illustrating interfaces according to an embodiment.

DETAILED DESCRIPTION

Figure 1:
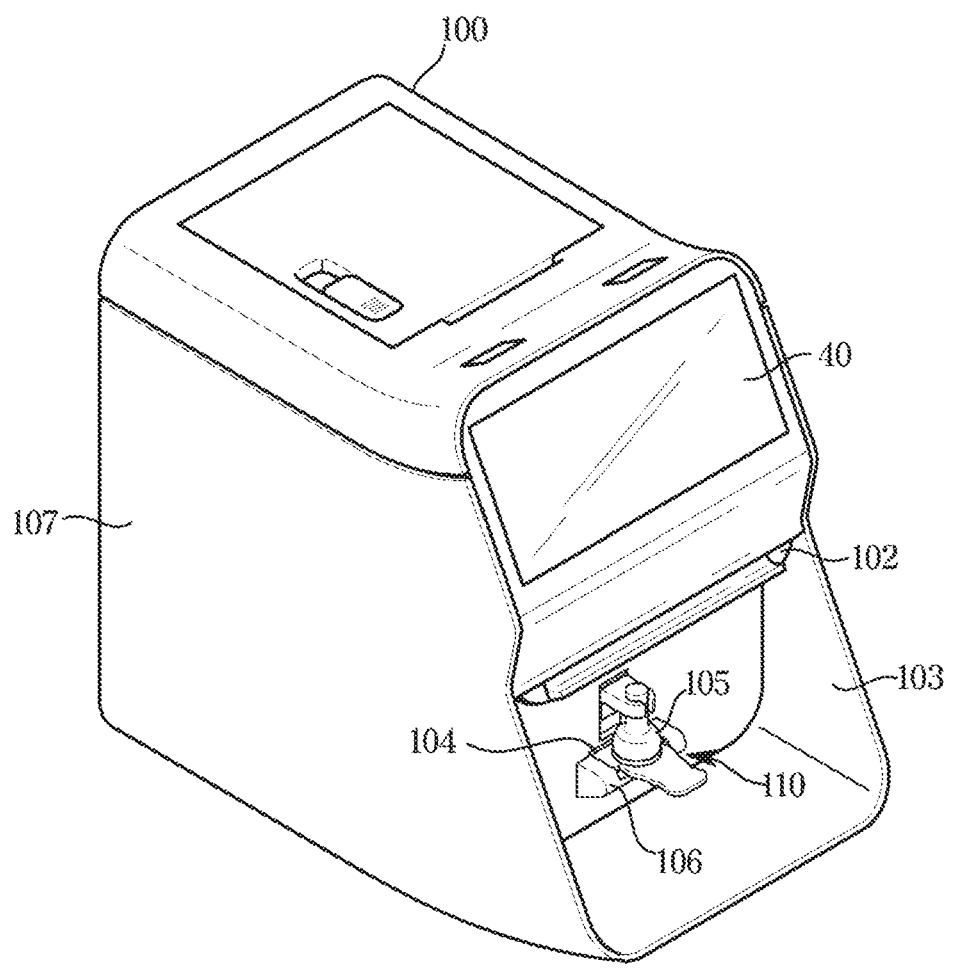
FIG. 1 is a perspective view illustrating the external appearance of a blood testing apparatus according to an embodiment.

In the following description of the disclosure, the same or similar elements are denoted by the same reference numerals even though they are depicted in different drawings. In the following description of the disclosure, all elements of the embodiments are not described, and a detailed description of general elements in the art or redundant elements in the embodiments will be omitted when it may make the subject matter of the disclosure rather unclear. Terms "part", "module", "member", and "block" used in the following description may be implemented as software or hardware, and a plurality of parts, modules, members, or blocks may be implemented as one element or one part, module, member or block may include a plurality of elements.

In the following description of the disclosure, it will be understood that, when a part is "connected to" another part, it can be directly connected to the other part or be indirectly connected to the other part, and indirect connection includes connection through a wireless communication network.

In addition, it will be understood that, when a part "includes" an element, the part may further include other elements and does not exclude presence of the elements, unless stated otherwise.

It will be understood that terms, such as "first", "second", etc., are used to distinguish one element from other elements and these elements should not be limited by these terms.

It will be understood that a singular expression may include a plural expression, unless there is a contextually clear exception.

Identification marks given to respective operations are used only for convenience of description and do not represent order among the respective operations, and the respective operations may be executed in a different order than described herein, unless a specific order is contextually clearly described.

In addition, "users" in the specification may be medical experts, i.e., a doctor including a veterinarian, a nurse, a medical image specialist, etc., without being limited thereto.

Expressions such as "at least one of," when preceding a list of elements, modify the entire list of elements and do not modify the individual elements of the list. For example, the expressions "at least one of a, b, and c" and "at least one of a, b, or c" should be understood as including only at least one a, only at least one b, only at least one c, both at least one a and at least one b, both at least one a and at least one c, both at least one b and at least one c, or all of at least one a, at least one b, and at least one c.

Figure 2:
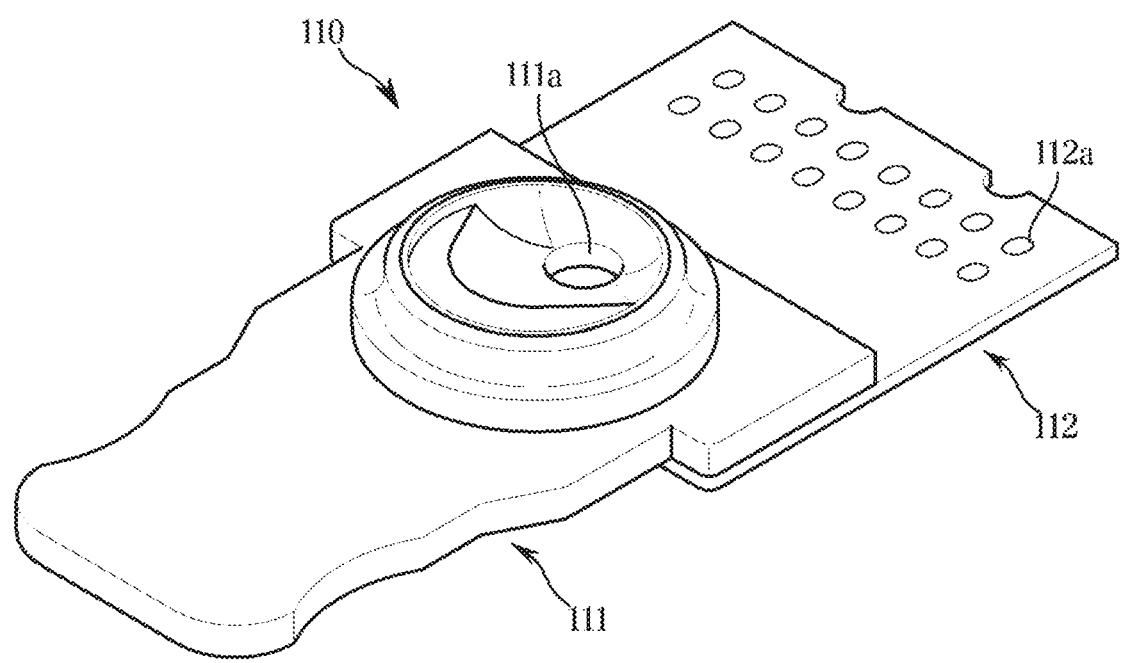
FIG. 2 is a perspective view of a test medium inserted into the blood testing apparatus of FIG. 2.
Figure 3:
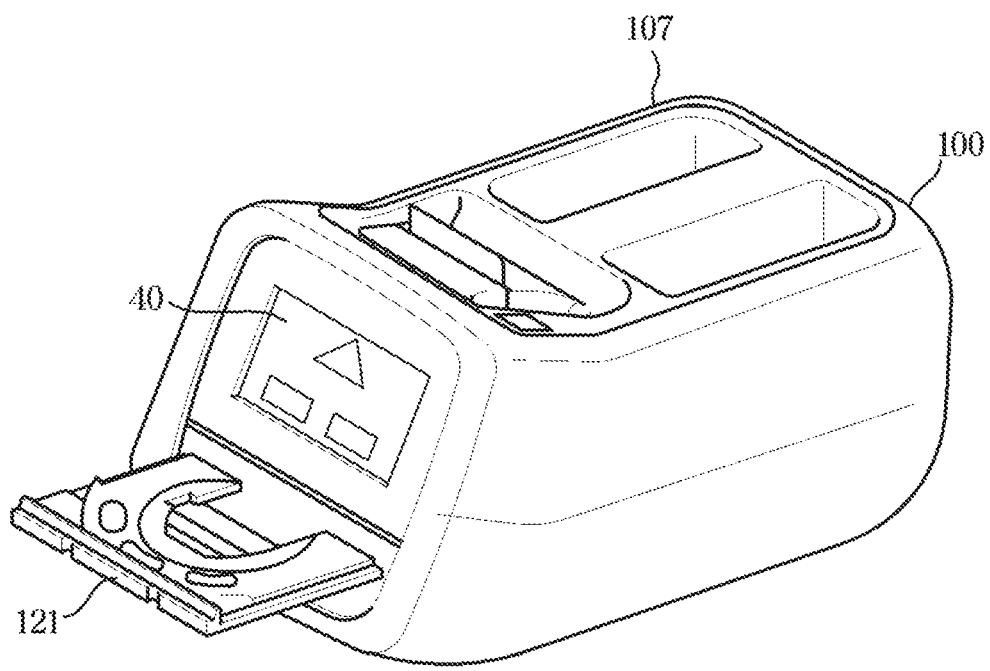
FIG. 3 is a perspective view illustrating the external appearance of a blood testing apparatus according to an embodiment.

FIG. 1 is a perspective view illustrating the external appearance of a blood testing apparatus according to an embodiment, FIG. 2 is a perspective view of a test medium inserted into the blood testing apparatus of FIG. 2, and FIG. 3 is a perspective view illustrating the external appearance of a blood testing apparatus according to an embodiment.

Referring to FIG. 1, a blood testing apparatus 100 is provided with a mount 103 serving as a space configured to receive a test medium 110 including blood taken from an animal. When a door 102 of the mount 103 is slid upwards to be opened, the test medium 110 may be mounted in the blood testing apparatus 100. As an example, a part of the test medium 110 may be inserted into an insertion groove 104 provided on the mount 103.

The part of the test medium 110 may be inserted into a main body 107, and the remainder may be exposed to the outside of the blood testing apparatus 100 and be supported by a support 106. When a pressurizer 105 applies pressure to the test medium 110, the pressurizer 105 may promote movement of the blood to an area in which the blood reacts with a reagent.

When mounting of the test medium 110 is completed, the blood testing apparatus 100 closes the door 102 and starts a test.

The test medium 110 inserted into the blood testing apparatus 100 shown in FIG. 1 may be a cartridge type and have an external appearance shown in FIG. 2.

Referring to FIG. 2, a housing 111 serves to support a platform 112 and to allow a user to grasp the test medium 110. The platform 112 may be joined to a lower part of the housing 111 or inserted into a groove formed on the housing 111, thus being coupled with the housing 111.

The housing 111 may be formed of a material which is easily molded and chemically and biologically inert. For example, various materials including acryl such as polymethyl methacrylate (PMMA), polysiloxane such as polydimethylsiloxane (PDMS), polycarbonate (PC), polyethylene such as linear low density polyethylene (LLDPE), low density polyethylene (LDPE), medium density polyethylene (MDPE), and high density polyethylene (HDPE), a plastic material such as polyvinyl alcohol, very low density polyethylene (VLDPE), polypropylene (PP), acrylonitrile butadiene styrene (ABS), and cyclic olefin copolymer (COC), glass, mica, silica, a semiconductor wafer, etc., may be used as materials for the housing 111.

An inlet hole 111a through which a sample is introduced into the housing 111 is formed in the housing 111. A user may drop a test object, i.e., blood, into the inlet hole 111a using a tool, such as a dropping pipette or a spuit.

A plurality of chambers 112a are formed on the platform 112, and a reagent is received in the chambers 112a. For example, a reagent may be applied to the insides of the chambers 112a and then dried. The blood having flowed into the inlet hole 111a reaches the chambers 112a through channels connecting the inlet hole 111a to the chambers 112a and reacts with the reagent received in advance in the chambers 112a. As described above in reference to FIG. 1, a part of the test medium 110 is inserted into the groove 104 of the blood testing apparatus 100. Reaction between the reagent and the blood occurs in the chambers 112a and, thus, the platform 112 may be inserted into the groove 104, and the pressurizer 105 may apply pressure to the inlet hole 111a to promote inflow of the sample.

The test medium 110 according to an embodiment may be a disc type and may be inserted into a blood testing apparatus 100 shown in FIG. 3.

Referring to FIG. 3, the blood testing apparatus 100 according to an embodiment may include a loader 121 configured to receive the disc-type test medium 110 and, when the disc-type test medium 110 is placed on the loader 121 and a user inserts the loader 121 into a main body 107, the test medium 110 is moved to the inside of the main body 107.

In the disc-type test medium 110 inserted into the main body 107, blood is moved by centrifugal force and thus may react with a reagent.

In addition to the disc type, the test medium 110 may be implemented as various types, such as a cuvette type in which a sample or a reagent is not moved and measurement is immediately carried out.

The blood testing apparatus 100 according to an embodiment may include a display 40 to display kinds, i.e., types, and analysis results (concentrations) of blood components acquired by analyzing the blood taken from the animal. The user may confirm the kinds of the respective blood components and the analysis results through the display 40.

Further, the display 40 may output a species of the animal, which the blood testing apparatus 100 determines using the blood components.

Figure 4:
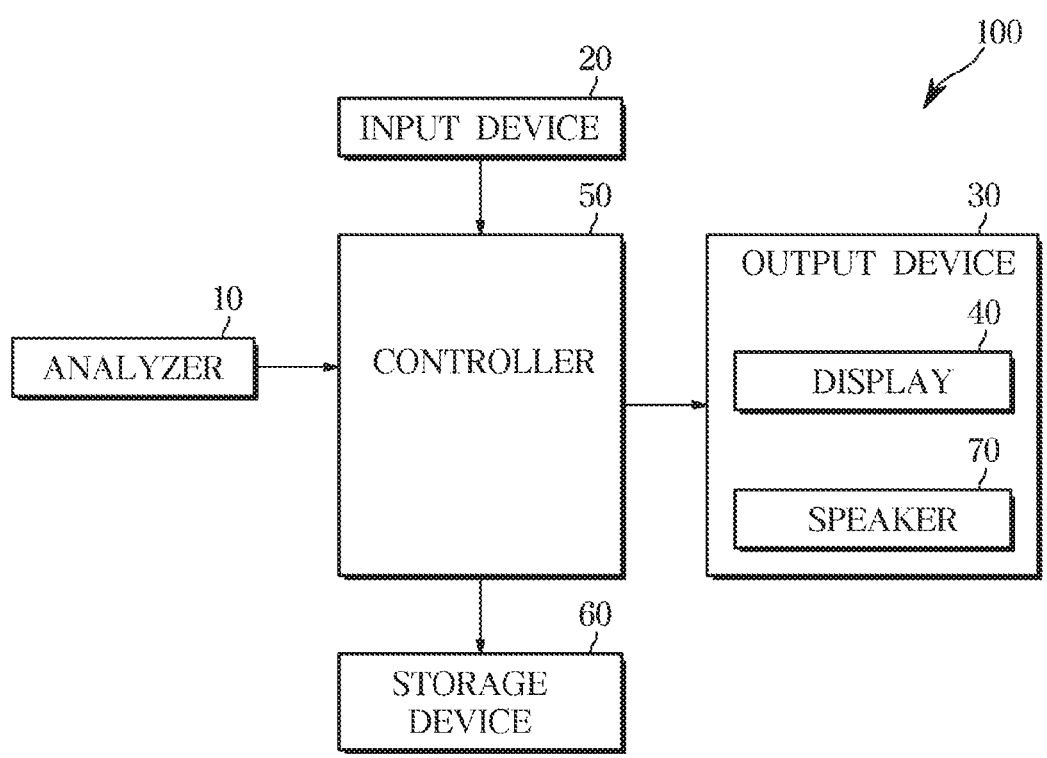
FIG. 4 is a control block diagram of the blood testing apparatus according to an embodiment.

FIG. 4 is a control block diagram of the blood testing apparatus 100 according to an embodiment.

Referring to FIG. 4, the blood testing apparatus 100 includes an analyzer 10 configured to analyze blood taken from an animal and acquire blood components, an input device 20 configured to receive various input information including a species of the animal from a user, a controller 50 configured to determine the species of the animal based on the blood components transmitted from the analyzer 10, a storage device 60 configured to store various data, such as a determination result of the controller 50, and an output device 30 configured to output analysis results and the determined species of the animal.

In more detail, the analyzer 10 may analyze components of the blood included in the test medium 110.

Blood includes various components including red blood cells, white blood cells, plasma, and platelets. The analyzer 10 analyzes the blood sample and thus analyzes which components are included in the blood and what are the amounts of the components.

Hereinafter, analysis result values (concentrations) according to the kinds of the respective blood components will be referred to as analysis results of the blood components.

The input device 20 receives an input command from the user.

There may be various input commands. In more detail, the user may transmit information regarding power on/off, test start/end, the species of the animal, etc. to the blood testing apparatus 100 through the input device 20.

A related art blood testing apparatus receives input information regarding an object, from which blood included in the test medium 110 is taken, from a user or the outside. In contrast, the blood testing apparatus 100 according to an embodiment determines a species of the animal through kinds of blood components and analysis results of the blood components of the analyzer 10, although the user inputs an incorrect species of the animal to the blood testing apparatus 100 through the input device 20, thus preventing user's misdiagnosis.

The input device 20 may include a hardware device including a mouse, a keyboard, a joystick, or hard keys configured to input specific data so as to receive input information from the user.

Further, the input device 20 may include a hardware device having software installed therein, i.e., a graphical user interface (GUI), such as a touch pad. The touch pad may be implemented as a touchscreen panel (TSP) and thus the touch pad and the display 40 may form a layered structure.

The output device 30 may include the display 40 configured to display the above-described various visual information and a speaker 70 configured to output auditory information.

The display 40 may be provided as a cathode ray tube (CRT), a digital light processing (DLP) panel, a plasma display panel, a liquid crystal display (LCD) panel, an electroluminescent (EL) panel, an electrophoretic display (EPD) panel, an electrochromic display (ECD) panel, a light emitting diode (LED) panel, or an organic light emitting diode (OLED) panel, without being limited thereto.

When the display 40 is implemented as a touchscreen panel (TSP) forming a layered structure with the touch pad, the display 40 may be used as the input device 20.

The output device 30 may display the analyzed blood components and output the species of the animal determined based on the blood components. When the determined species of the animal is not the same as the species of the animal included in the input information input by the user, i.e., they do not coincide, the output device 30 may output various interfaces configured to induce the user to change the species of the animal.

The speaker 70 is a device configured to output various sounds communicating with the user under the control of the controller 50 and, for example, when the species of the animal determined by the controller 50 does not coincide with the species of the animal included in the input information input by the user, the speaker 70 may output an alarm.

The speaker 70 may output various predetermined sounds during operation of the blood testing apparatus 100.

The controller 50 may control the overall operation of the blood testing apparatus 100.

In more detail, the controller 50 controls the analyzer 10 to analyze blood components in the blood of the animal and displays analysis results through the output device 30. Further, the controller 50 determines the species of the animal based on the analyzed kinds of the blood components and the analysis results of the blood components.

Determination of the species of the animal by the controller 50 is based on a learning model by machine learning for the kinds and analysis results of the blood components.

The controller 50 controls the output device 30 to output an interface configured to induce the user to change the input species of the animal (e.g., inform the user that the species was incorrectly entered and prompt, request, or ask the user to change the input species of the animal), when the determined species of the animal does not coincide with the species of the animal input by the user. When the user inputs the species of the animal through the input device 20, correction is performed based on the changed species of the animal using raw data used for previous analysis. Therethrough, the blood testing apparatus 100 does not execute analysis twice or more and outputs analysis results, thus promoting efficiency.

The controller 50 may compare the species of the animal input by the user with a species of the animal included in at least one of a barcode, a QR code, an RFID tag, and a USB chip which are included in the test medium 110. When the species of the animal do not coincide with each other, the controller 50 controls the output device 30 to output an interface configured to induce the user to change the input information prior to execution of analysis.

The controller 50 may be implemented as a memory configured to store algorithms configured to control the elements of the blood testing apparatus 100 or data regarding programs reproducing the algorithms, and a processor configured to perform the above-described operation using the data stored in the memory. The memory and the processor may be respectively implemented as separate chips, or the memory and the processor may be implemented as a single chip.

The storage device 60 may store data including the analysis results of the blood components transmitted from the analyzer 10, the determination result regarding the species of the animal determined by the controller 50 and various algorithms for operation of the blood testing apparatus 100.

The storage device 60 may store data for machine learning, e.g., analysis results of various animal species. For example, the storage device 60 stores animal species determined according to different machine learning with respect to the blood included in the inserted test medium 110, and the controller 50 compares them, thus finally determining the species of the animal which is being currently analyzed.

Further, the storage device 60 temporarily stores results of previous analysis executed to determine a species of the animal and raw data used in the analysis. When the user changes the species of the animal, the storage device 60 transmits the stored raw data to the controller 50.

The storage device 60 may be implemented as at least one of a non-volatile memory, such as a cache, a Read Only Memory (ROM), a Programmable ROM (PROM), an Erasable Programmable ROM (EPROM), an Electrically Erasable Programmable ROM (EEPROM) or a flash memory, a volatile memory, such as a Random Access Memory (RAM), and a storage medium, such as a Hard Disk Drive (HDD) or a CD-ROM, without being limited thereto. The storage device 60 may be a memory implemented as a chip provided separately from the above-described processor of the controller 50, or the storage device 60 and the processor of the controller 50 may be implemented as a single chip.

The blood testing apparatus 100 may further include various elements, such as a communication interface communicating with the outside and is not limited to the above-described elements shown in FIG. 4.

Figure 5:
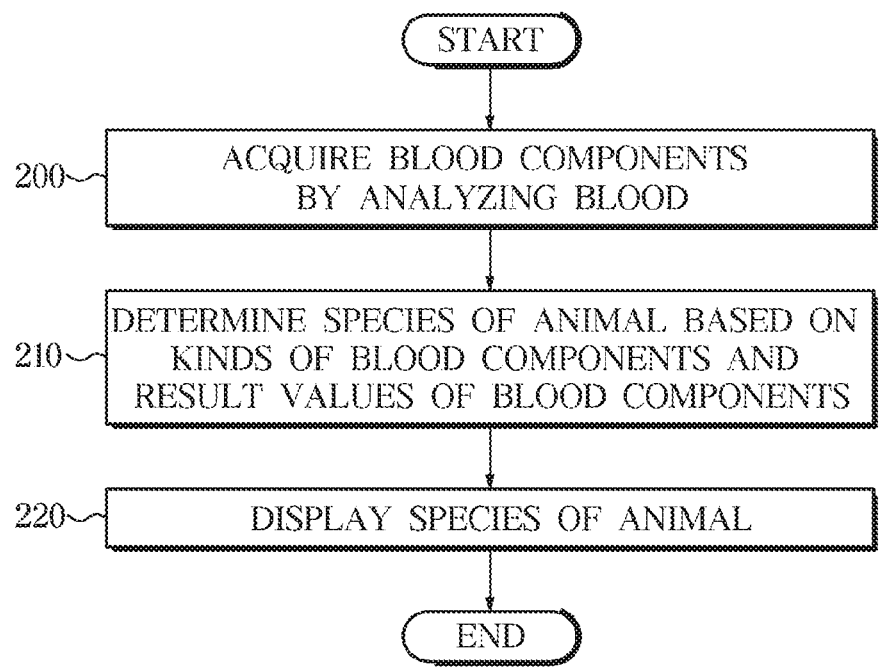
FIG. 5 is a flowchart illustrating the operation of the blood testing apparatus according to an embodiment.

FIG. 5 is a flowchart illustrating the operation of the blood testing apparatus according to an embodiment.

Referring to FIG. 5, the blood testing apparatus 100 acquires blood components by analyzing blood included in the test medium 110 (operation 200).

The blood components include kinds of the blood components and analysis results according to the respective kinds of the blood components.

For example, the blood testing apparatus 100 may analyze various components, such as albumin (ALB), alkaline phosphatase (ALP), alanine aminotransferase (ALT), aspartate aminotransferase (AST), creatinine (CREA), gamma glutamyl peptidase (GGT), etc., as blood components of an animal, and the analysis results according to the kinds of the respective blood components, i.e., concentrations of the respective blood components, may be displayed.

Particularly, the blood testing apparatus 100 acquires raw data regarding the respective components from the blood. The raw data includes kinds of the blood components and initial concentrations of the blood components. The blood testing apparatus 100 performs correction of the acquired raw data based on an inner temperature of the blood testing apparatus 100 at the time of analysis, setting information of the test medium 110, and other setting information. Thereafter, the blood testing apparatus 100 performs correction again based on information regarding an input species of the animal and then outputs final analysis results.

The blood testing apparatus 100 determines a species of the animal based on the analyzed kinds of the blood components and the analysis results of the blood components (operation 210).

The blood testing apparatus 100 determines the species of the animal based on a learning model obtained through machine learning. In more detail, the learning model compares the analysis results according to the kinds of the blood components with predetermined reference values regarding the species of the animal. A comparison process may include a decision tree or deep learning in which machine learning is executed through an artificial neural network (ANN).

When the blood testing apparatus 100 determines the species of the animal, the blood testing apparatus 100 displays the determined species of the animal through the output device (operation 220).

For example, the blood testing apparatus 100 may determine the species of the animal which is subjected to analysis as Canidae or Canine based on analyzed blood components of the animal in a cartridge A, as exemplarily shown in interface 1002 of FIG. 10. The blood testing apparatus 100 may display an interface configured to output the determined species of the animal through the display 40 and request confirmation from the user.

Figure 6:
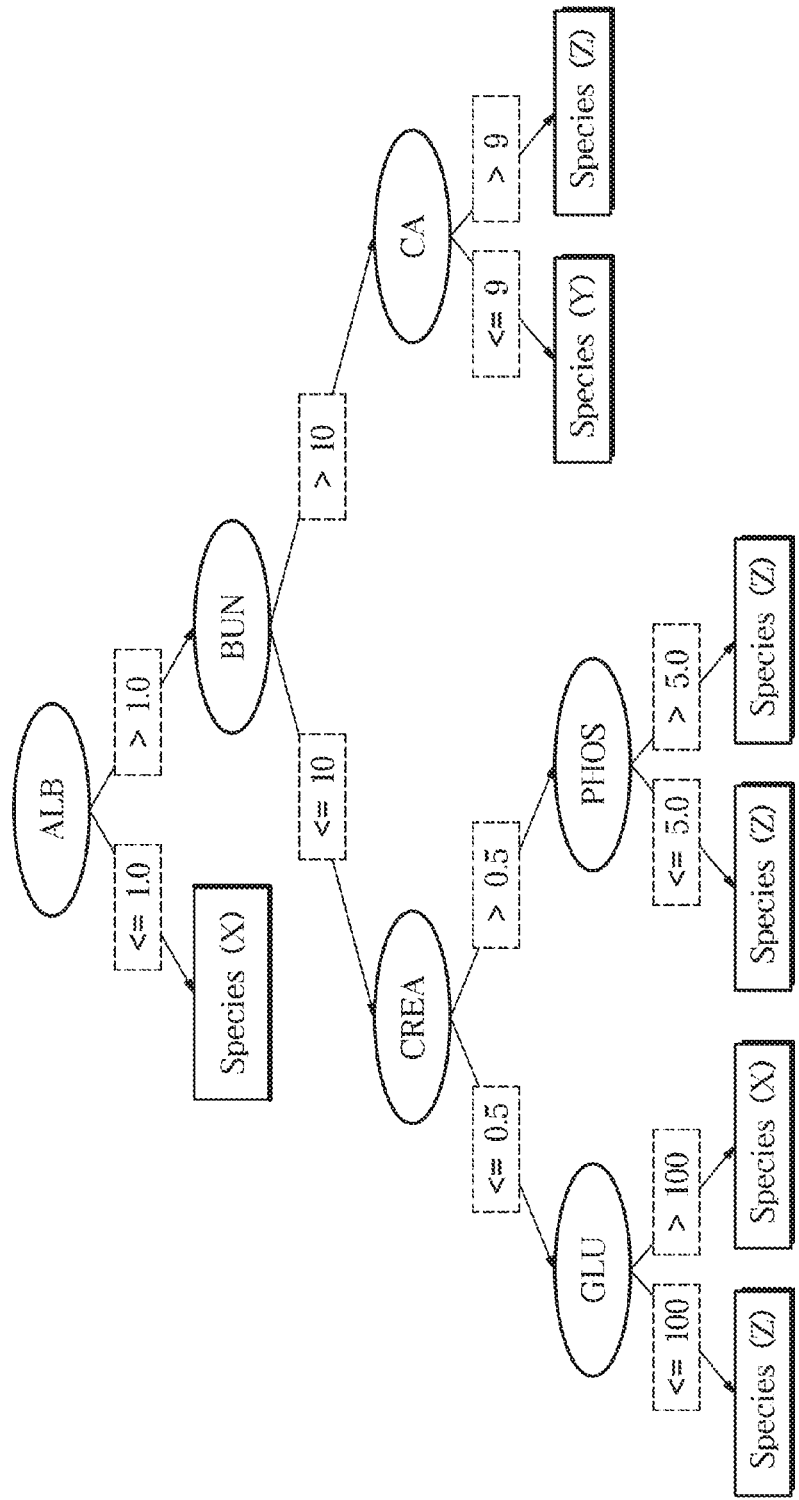
FIGS. 6 and 7 are views each illustrating methods of determining a species of an animal using the blood testing apparatus according to an embodiment.
Figure 7:
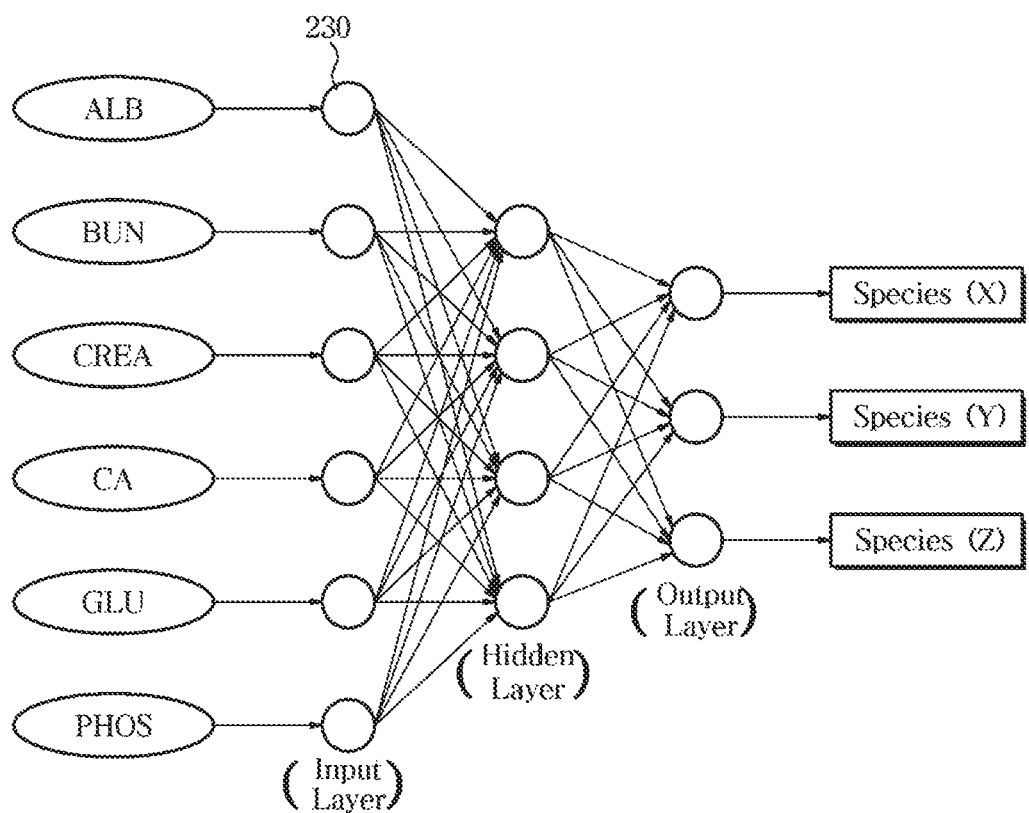

FIGS. 6 and 7 are views each illustrating methods of determining a species of an animal using the blood testing apparatus according to an embodiment.

Referring to FIG. 6, the blood testing apparatus 100, particularly, the controller 50, may determine the species of the animal according to a decision tree of learning models stored in the storage device 60. The controller 50 compares analyzed kinds of blood components and analysis results according to the kinds of the blood components with predetermined reference values, and predicts the species of the animal in set order based on comparison results.

For example, when the analyzed blood components include ALB and the analysis result of ALB is less than 1.0, the controller 50 may determine the species of the animal, the blood of which is included in the test medium 110, as X. However, when the analysis result of ALB is more than 1.0, the controller 50 may compare an analysis result of another blood component, for example, blood urea nitrogen (BUN), with a predetermined reference value.

After determination of the analysis result of ALB, when the kinds of the analyzed blood components do not include BUN, the controller 50 may determine the species of the animal using another decision tree stored on the storage device 60.

The decision tree shown in FIG. 6 is one example of the determination process of the controller 50, and the kinds of the blood components including ALB, BUN, cancer antigen (CA), glucose (GLU), and phosphorus (PHOS) and respective reference values thereof may be variously changed.

A controller 50 according to an embodiment may determine the species of the animal from which the blood sample is collected through deep learning.

Deep learning is a method of machine-learning data by classifying (or clustering) a previous determination process and analysis results not based on predetermined reference values. That is, in deep learning, several layers are placed on a plurality of pieces of data to be classified, the data is labeled, the labeled data is updated while comparing with analysis results to be determined, and the updated data is applied to a next determination process.

Referring to FIG. 7, the controller 50 inputs a plurality of analyzed kinds of blood components and analysis results thereof to respective nodes included in an input layer. The respective nodes included in the input layer may include variable weights. That is, the weights are labeled data, and the weights are continuously adjusted so that the analysis results input to the input layer reach a predicted species of the animal.

When a blood component ALB is input to the first node 230, the weight predetermined in the first node 230 and the analysis result of ALB are input to an activation function. A result, i.e., an output value, of the activation function becomes a final output value of the first node 230 (a first output value).

Respective first output values output from the respective nodes of the input layer are input again to nodes included in a hidden layer and are applied to activation functions provided in the respective nodes of the hidden layer, thus calculating output values (second output values). Here, weights of the nodes included in the hidden layer may differ from the weight of the node included in the input layer.

Although FIG. 7 illustrates one shallow hidden layer, the controller 50 according to an embodiment may transmit the output values of the respective nodes to an output layer through two or more hidden layers and determine the species of the animal by finally putting output values output from activation functions of respective nodes included in the output layer together.

Through the weights determined through the above-described process, the controller 50 adjusts the weights again based on new blood components and a species of an animal acquired thereby as output values. In machine learning, the method of identifying the species of the animal according to other new input components is continuously learned through such continual updates.

The controller 50 may extract features of components of a blood sample and input the extracted features to the input layer. That is, learning effects may be enhanced by continuously updating the values of the input nodes through the machine learning rather than adjusting the values by the user. That is, the controller 50 may more accurately determine a species of an animal according to blood components of a next input using previously analyzed weights.

The methods of determining a species of an animal shown in FIGS. 6 and 7 are examples of determination of a species of an animal using the blood testing apparatus 100, and a species of an animal may be variously determined.

For example, the blood testing apparatus 100 may compare a species of an animal determined through the decision tree shown in FIG. 6 and a species of the animal determined through deep learning and thus finally determine the species of the animal. That is, the blood testing apparatus 100 may determine the species of the animal by storing the species of the animal determined based on whether or not analysis results of blood components are more than reference values (a first determination result) in the storage device 60 and then comparing the first determination result with the species of the animal determined through feature extraction (a second determination result).

In the blood testing apparatus 100, when blood taken from the same test object, for example, an animal having the same pet ID shown in FIG. 10, is tested using different test media, previous test results may be used to determine a species of the animal. That is, the controller 50, although kinds of blood components analyzed through a currently inserted test medium (a second cartridge) differs from kinds of blood components analyzed through a first cartridge, may determine the species of the animal based on the blood components extracted from the first cartridge and the blood components extracted from the second cartridge, which has different kinds from those of the blood components extracted from the first cartridge.

Figure 8B:
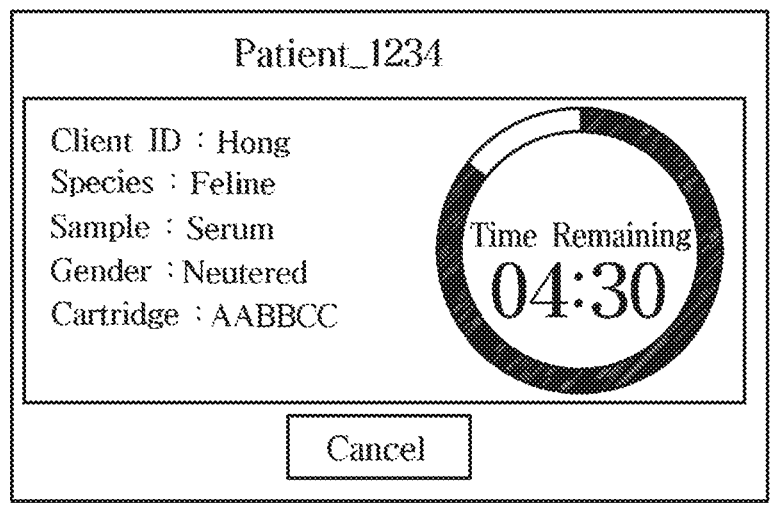

FIGS. 8A to 8C are views of exemplary interfaces illustrating problems of a related art blood testing apparatus.

The blood testing apparatus displays an interface configured to input information about a species of an animal, as exemplarily shown in FIG. 8A. The user inputs, for example, Feline, as the species of the animal through an input device, instead of Canine. When the user inputs OK into the interface to execute analysis, the blood testing apparatus executes analysis based on the input species of the animal (FIG. 8B).

After execution of analysis, the blood testing apparatus displays analysis results based on the input species of the animal, i.e., Feline, as exemplarily shown in FIG. 8C. Thus, the blood testing apparatus displays the analysis results based on the incorrectly input species of the animal but cannot correct the species of the animal. Therefore, the user has to input a species of the animal again, into the interface shown in FIG. 8A, and then analysis is executed again for 4 minutes or more, thereby causing inconvenience and lost work time.

FIG. 9 is a flowchart illustrating a method of inducing change of an input species of an animal according to an embodiment. FIGS. 10, 13A and 13B exemplarily illustrate interfaces configured to induce change of the species. A detailed description of redundant elements of the interfaces which are the same as those of the interfaces shown in FIGS. 8A to 8C will be omitted.

Referring to FIG. 9, the blood testing apparatus 100 according to an embodiment receives input information from a user (operation 300).

The input information may include an identification (ID) number to identify a currently inserted test medium 110, a name, blood type, gender, age, weight, height, and species of an animal, as exemplarily shown in interface 1000 of FIG. 10 and/or interface 1010 of FIG. 13A.

The blood testing apparatus 100 executes analysis based on the input information and determines the species of the animal based on analysis results (operation 310).

The analysis results include kinds of blood components and analysis results (concentrations) of the blood components. Further, the blood testing apparatus 100 according to an embodiment determines the species of the animal based on the analysis results, as described above with reference to FIG. 5.

The blood testing apparatus 100 compares the determined species of the animal with the species of the animal received by the input device 20 (operation 320).

In operation 330, when the determined species of the animal coincides with the species of the animal received by the input device 20, i.e., they are the same, the blood testing apparatus 100 outputs the determined species of the animal (operation 350).

When the determined species of the animal does not coincide with the species of the animal received by the input device 20, the blood testing apparatus 100 induces the user to change the input information (operation 340).

As one example, the blood testing apparatus 100 may list kinds of blood components and display analysis results of the blood components, as exemplarily shown in interface 1002 of FIG. 10. Further, the blood testing apparatus 100 may display the determined species of the animal based on the analysis results and output an interface configured to ask whether or not the user wants to change the species of the animal, together with a notification that the determined species of the animal does not coincide with the input information.

As another example, the blood testing apparatus 100 may display various examples of animal species and induce the user to choose one of them, as exemplarily shown in interface 1020 of FIG. 13B, for example, in response to user activating a button 1016 in FIG. 10 or a button 1018 in FIG. 13A. Although the species of the animal determined by the blood testing apparatus 100, i.e., Canine, is shown to be arranged at the uppermost position, the position of the determined species of the animal is not limited thereto.

When the user changes the species of the animal through the interface configured to induce the user to change the species, the blood testing apparatus 100 re-executes analysis again based on the changed input information. Interface 1022 of FIG. 13B illustrates one example of kinds of blood components and analysis results of the blood components acquired by re-executing analysis.

Figure 11:
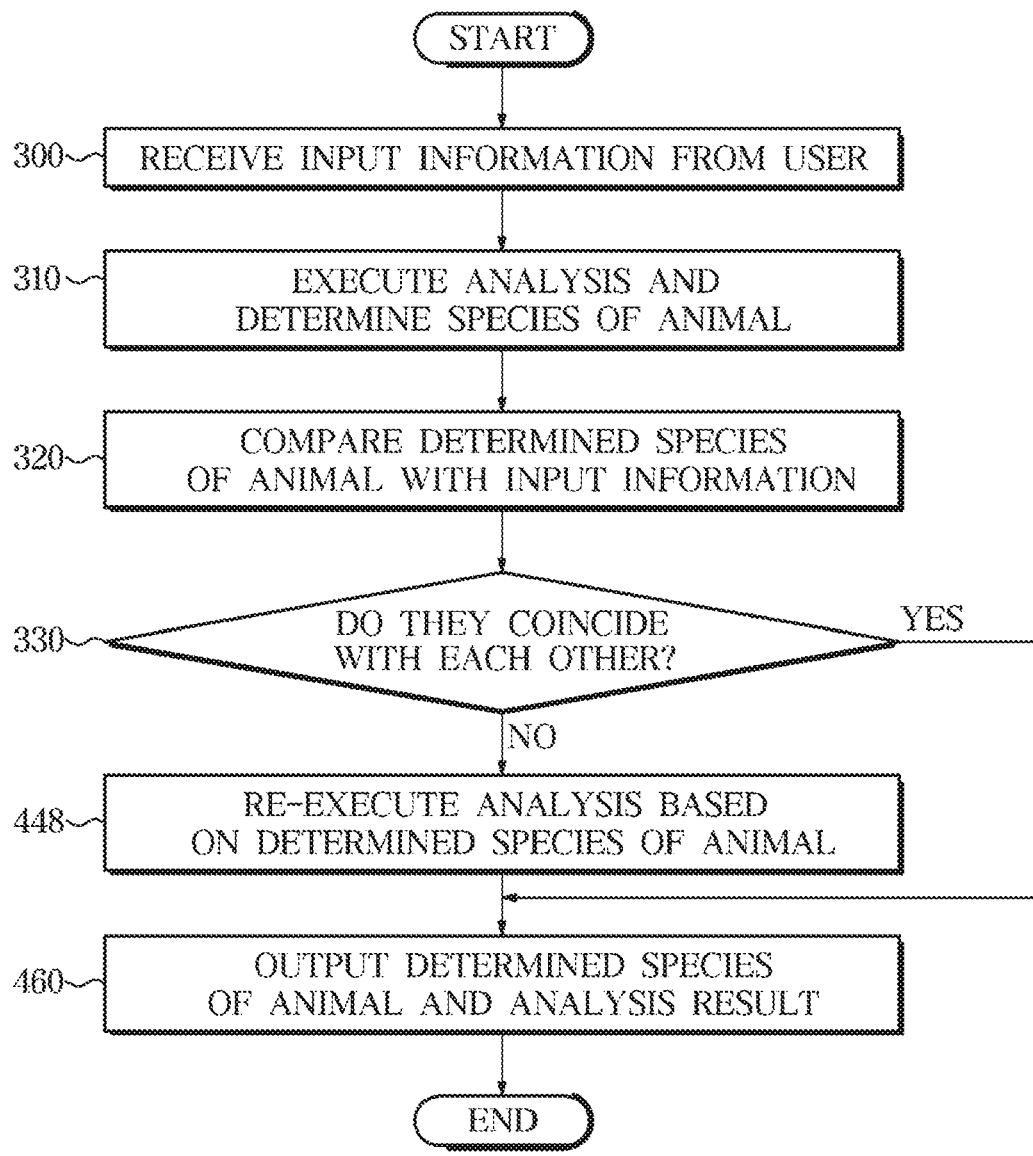
FIG. 11 is a flowchart illustrating a method of executing an analysis according to an embodiment.

FIG. 11 is a flowchart illustrating a method of executing analysis based on a determined species of an animal according to an embodiment differing from the embodiment of FIG. 9. A description of redundant particulars of the method which are the same as those of the method of FIG. 9 will be omitted.

Referring to FIG. 11, the blood testing apparatus 100 according to an embodiment receives input information from a user (operation 300). The blood testing apparatus 100 executes analysis based on a species of the animal included in the received input information, and determines a species of the animal based on analysis results (operation 310).

The blood testing apparatus 100 compares the determined species of the animal with the species of the animal received by the input device 20 (operation 320).

When the determined species of the animal coincides with the species of the animal received by the input device 20, the blood testing apparatus 100 outputs the determined species of the animal and the analysis results (operation 460).

When the determined species of the animal does not coincide with the species of the animal received by the input device 20, the blood testing apparatus 100 does not output an interface configured to induce the user to change the input information and may re-execute analysis based on the determined species of the animal (operation 448).

For example, the blood testing apparatus 100 does not induce the user to change the input species of the animal while displaying the determined species of the animal, and may immediately re-execute analysis based on the determined species of the animal.

In re-execution of analysis, the analyzer 10 may be operated newly and execute analysis. However, the disclosure is not limited thereto, and the blood testing apparatus 100 may re-execute only analysis in which correction relating to the species of the animal is carried out, and thus shorten a testing time.

When analysis is completed, the blood testing apparatus 100 may output analysis results acquired by executing analysis based on the determined species of the animal and output the determined species of the animal through the output device 30 (operation 460).

Figure 12:
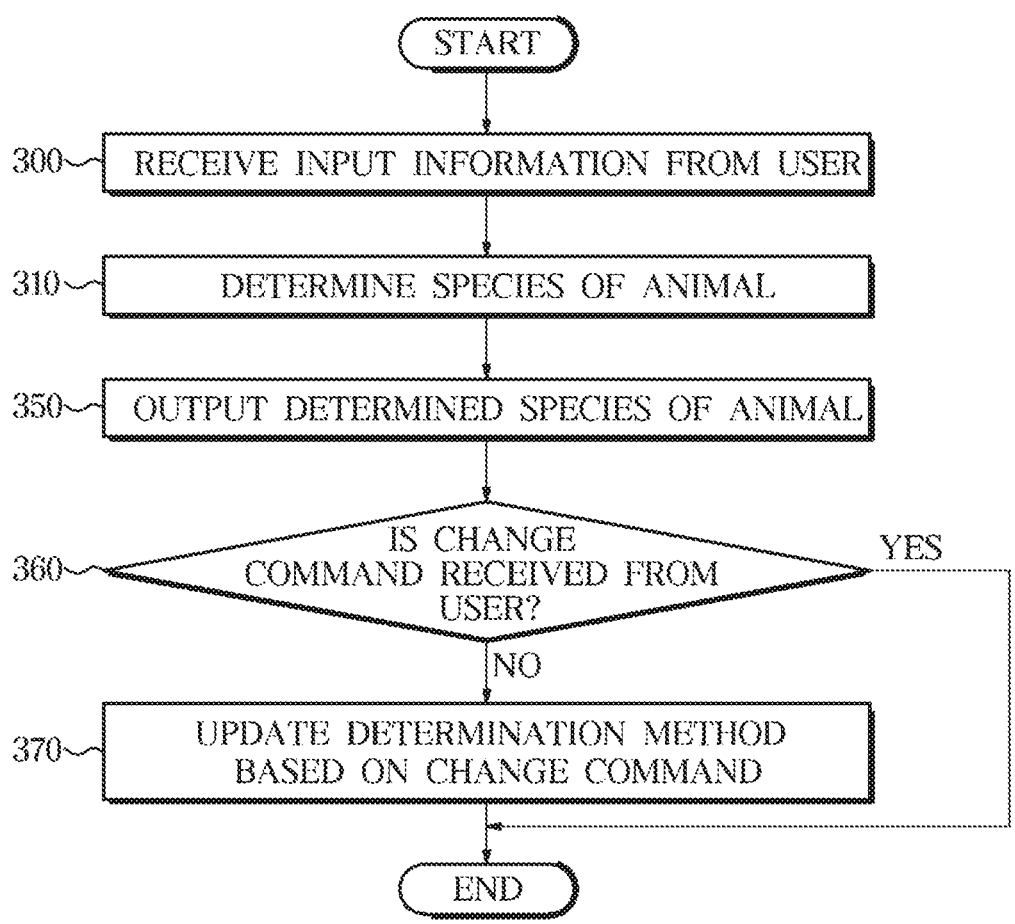
FIG. 12 is a flowchart illustrating a method of determining a species of an animal according to an embodiment.

FIG. 12 is a flowchart illustrating a method of determining a species of an animal according to an embodiment. A detailed description of operations of the method which are the same as those of the method of FIG. 11 will be omitted to avoid redundancy.

The blood testing apparatus 100 outputs a species of the animal determined based on analysis results (operation 350). When the determined species of the animal does not coincide with a species of the animal input by a user, the blood testing apparatus 100 outputs an interface configured to induce the user to change input information.

When a change command is received from the user operation 360: YES), the blood testing apparatus 100 re-executes analysis based on the changed species of the animal, as exemplarily shown in FIG. 9. However, when a change command is not received (operation 360: NO), the blood testing apparatus 100 updates the determination method (operation 370).

No input of a change command means that there is an error in the determination method of the blood testing apparatus 100.

When the determination method is based on machine learning, the blood testing apparatus 100 may change weights based on the error and then update the determination method. When the determination method is based on a decision tree, the blood testing apparatus 100 adjusts reference values included the decision tree so that analyzed values of blood components is changed to be determined as the input species of the animal.

Thereby, the blood testing apparatus 100 according to an embodiment may increase accuracy in determination of a species of an animal.

Figure 15A:
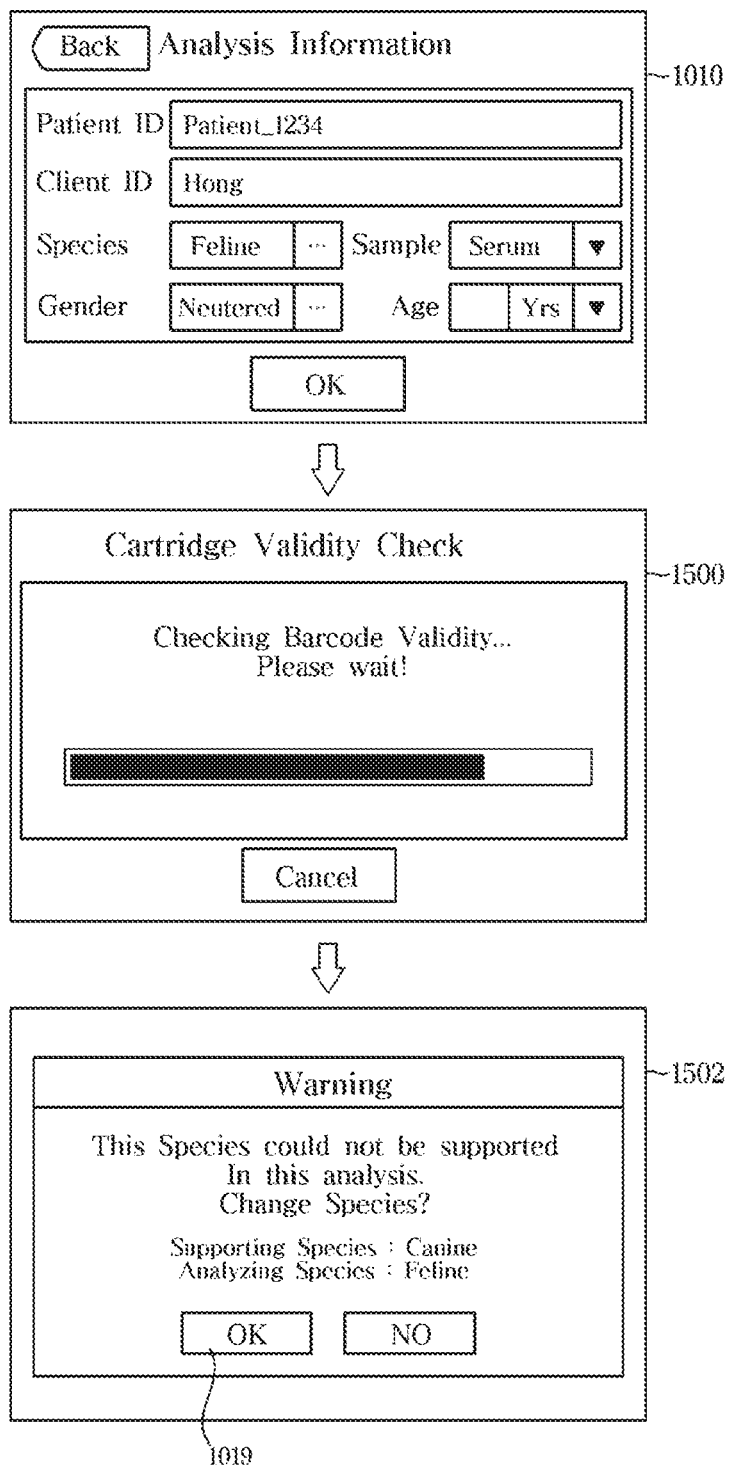

FIG. 14 is a flowchart illustrating a method of inducing change of a species of an animal according to an embodiment. FIGS. 15A and 15B are views exemplarily illustrating interfaces.

Referring to FIG. 14, the blood testing apparatus 100 receives input information including a species of the animal from a user (operation 400).

For example, the blood testing apparatus 100 may display interfaces shown in FIG. 15A through the display 40 and receive Feline as the species of the animal from the user.

The user may insert the test medium 110 into the main body 107 prior to or after input of the input information. For example, the test medium 110 may be provided as a cartridge, and data including blood information, such as a barcode, may be provided in the cartridge or on a package enclosing the cartridge.

The blood testing apparatus 100 may confirm information regarding the species of the animal through the test medium 110 (operation 410).

Interface 1500 of FIG. 15A exemplarily illustrates an interface displayed while, when the test medium 110 is a cartridge, information regarding the species of the animal included in the cartridge is extracted by reading a barcode included in the cartridge.

Information included in the test medium 110 may be provided in various types, such as a QR code, an RFID tag, and a USB chip configured to transmit information, in addition to the barcode, and the information included in the test medium 110 may be confirmed at the outside through the communication interface.

The blood testing apparatus 100 compares the input information with the confirmed species of the animal prior to analysis (operation 420).

In operation 430, when the input information coincides with the confirmed species of the animal, the blood testing apparatus 100 executes analysis (operation 450).

When the input information does not coincide with the confirmed species of the animal, the blood testing apparatus 100 may induce the user to change the input information (operation 440).

The blood testing apparatus 100 may output an interface including information that the input information does not coincide with the confirmed species of the animal through the display 40, as exemplarily shown in interface 1502 of FIG. 15A. The interface may display that the confirmed species of the animal is Canine and the species of the animal input by the user is Feline.

When the user clicks a button 1019 configured to change the species of the animal, the blood testing apparatus 100 may display an interface configured to display various animal species and to induce the user to choose one species, as exemplarily shown in interface 1510 of FIG. 15B.

When the user inputs a changed species of the animal, the blood testing apparatus 100 executes analysis based on the changed species of the animal. For example, the blood testing apparatus 100 may output an interface 1512 shown in FIG. 15B and inform the user that analysis is being executed.

When analysis is executed, the blood testing apparatus 100 outputs kinds of respective blood components and analysis results (concentrations) of the blood components, as exemplarily shown in interface 1514 of FIG. 15B. In more detail, an interface configured to display numerical values and units of the analyzed concentrations of the blood components and reference ranges of the analyzed concentrations of the blood components which may be determined as normal ranges in the changed species of the animal as the analysis results and display a warning about the blood components, the numeral values of the concentrations of which deviate from the normal ranges, may be provided to be useful for analysis of the user.

The interfaces shown in FIGS. 10, 13A, 13B, 15A, and 15B are just examples and may be variously changed.

Figure 16:
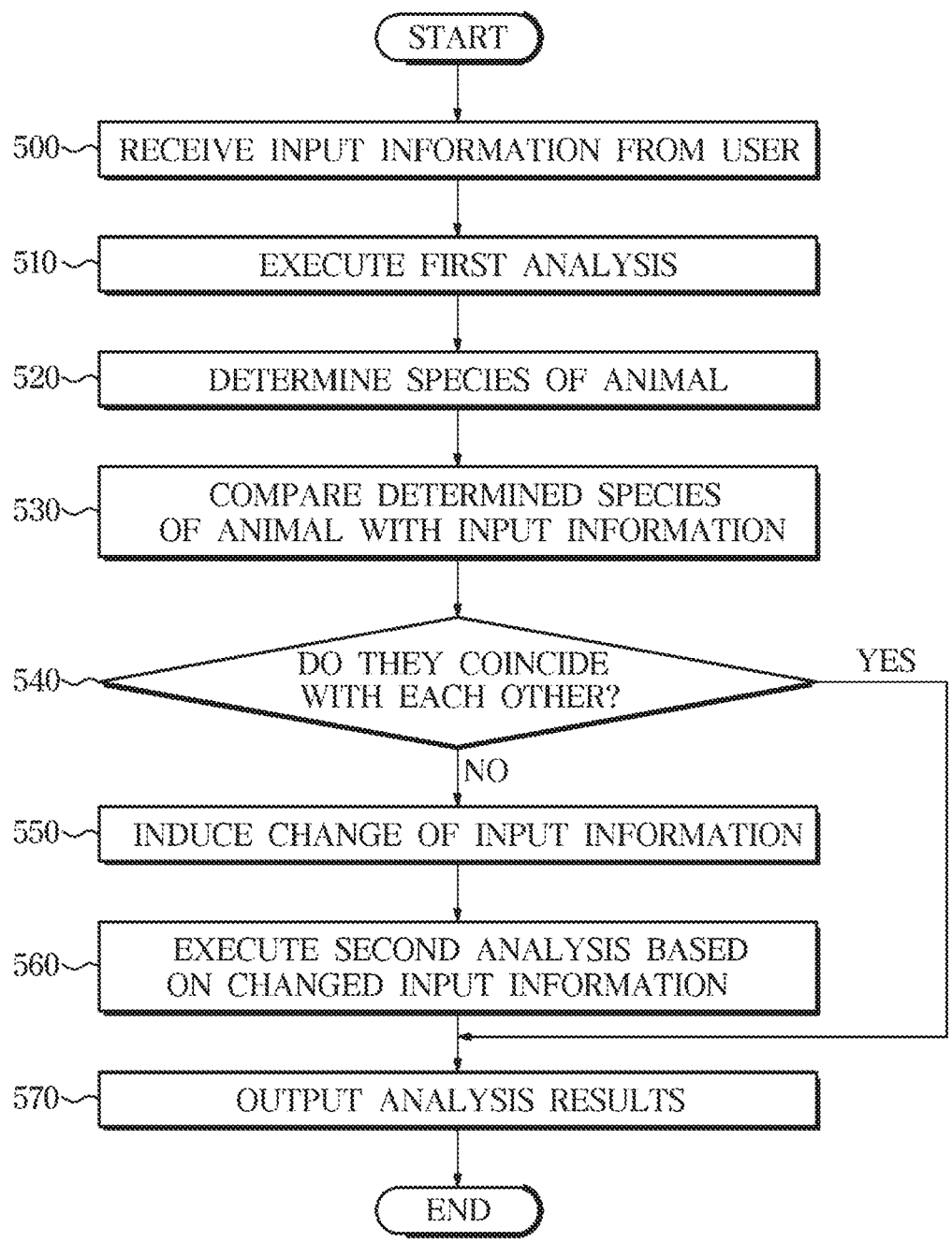
FIG. 16 is a flowchart illustrating a method of executing an analysis according to an embodiment.
Figure 20A:
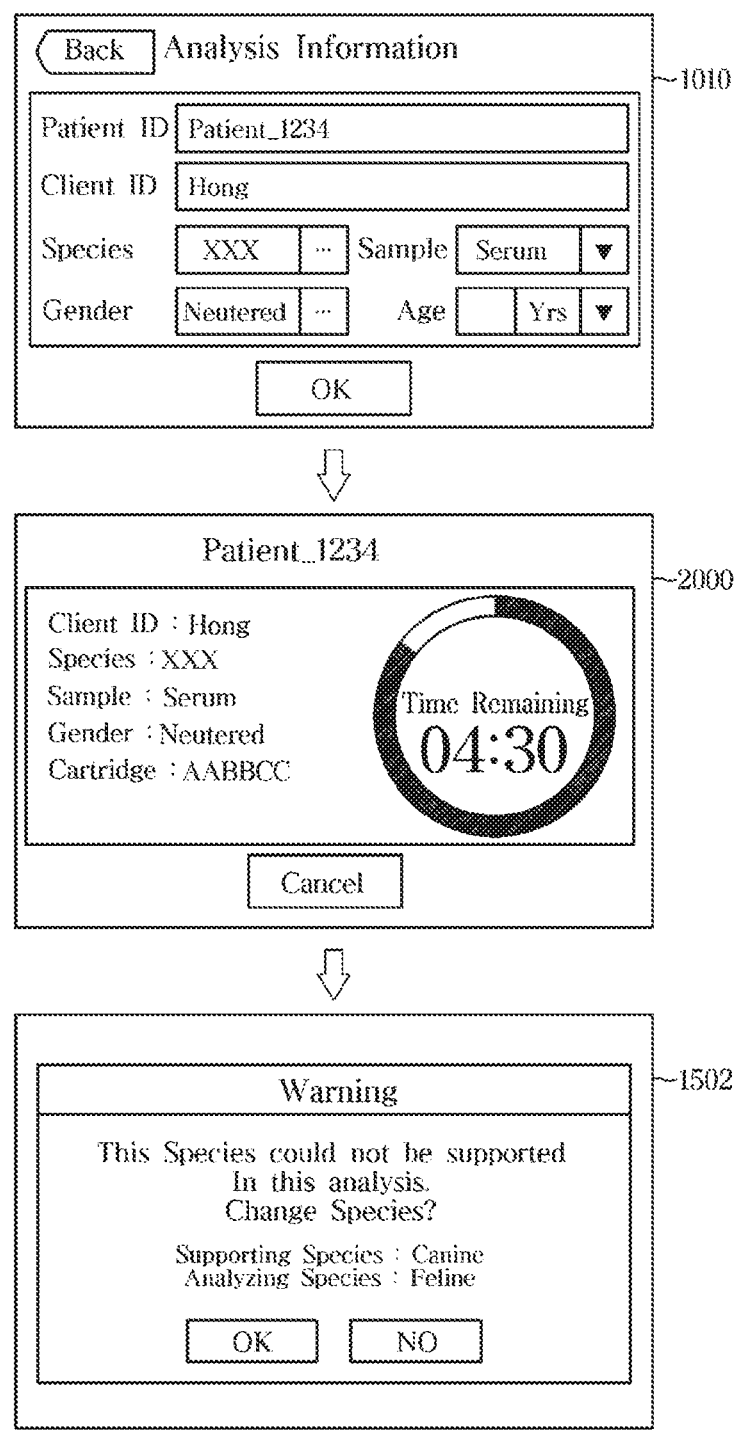

FIG. 16 is a flowchart illustrating a method of executing analysis after change of a species of an animal according to an embodiment. FIGS. 20A and 20B are views exemplarily illustrating interfaces.

In operation 500, input information is received from a user. The user inputs various pieces of information regarding blood included in the test medium 110, as exemplarily shown in interface 1010 of FIG. 20A. For example, the user may input Feline or Canine as information of the test medium 110 including blood of a Canine animal.

The blood testing apparatus 100 executes a first analysis (operation 510).

The first analysis is an analysis which is executed based on the species of the animal initially input by the user.

During execution of the first analysis, the blood testing apparatus 100 may output an interface 2000 shown in FIG. 20A and inform the user that analysis is being executed.

The blood testing apparatus 100 determines a species of the animal through kinds of blood components and analysis results thereof determined based on results of the first analysis in the same manner as the method shown in FIG. 5 (operation 520). Further, the blood testing apparatus 100 compares the species of the animal included in the input information with the determined species of the animal (operation 530).

In operation 540, when the species of the animal included in the input information coincides with the determined species of the animal, the blood testing apparatus 100 outputs the kinds of the blood components and analysis results thereof determined based on the first analysis through an interface 1514 shown in FIG. 20B (operation 570).

When the species of the animal included in the input information does not coincide with the determined species of the animal, the blood testing apparatus 100 outputs the determined species of the animal and induces the user to change the input information through an interface 1502 shown in FIG. 20A (operation 550).

For example, a species of the animal, the blood of which is actually included in the test medium 110, is Canine according to a determination result of the blood testing apparatus 100 and thus the determined species, Canine, does not coincide with the input information, i.e., Feline. Therefore, the user may change the input information through an interface output by the display 40, as exemplarily shown in interface 1510 of FIG. 20B. When the user changes the species of the animal into Canine, as exemplarily shown in FIG. 20B, the blood testing apparatus 100 executes a second analysis based on the changed input information (operation 560).

For example, during execution of the second analysis, the blood testing apparatus 100 may output an interface 2010 shown in FIG. 20B.

The blood testing apparatus 100 outputs analysis results based on the second analysis, as exemplarily shown in interface 1514 of FIG. 20B (operation 570).

Figure 17:
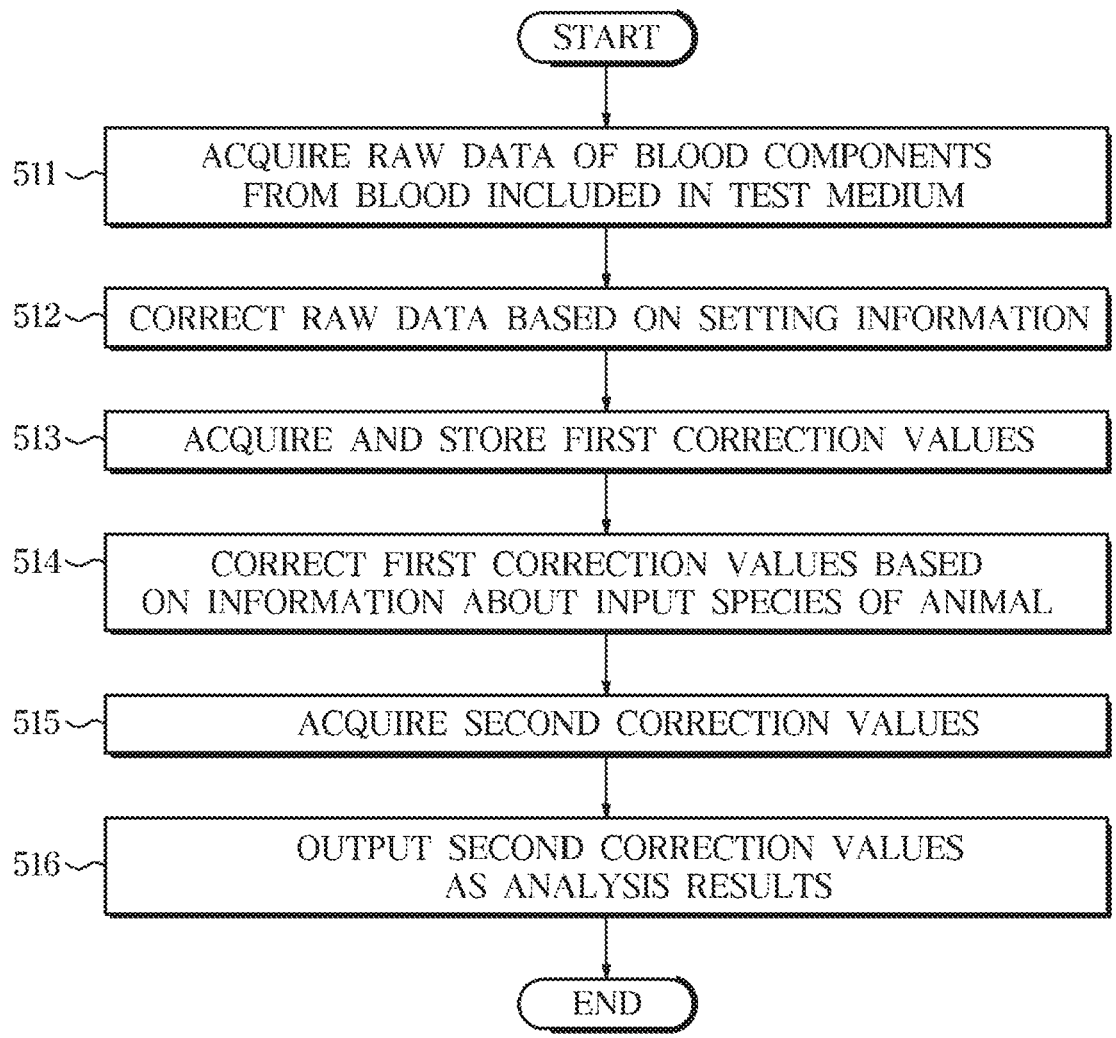
FIG. 17 is a flowchart illustrating an analysis according to an embodiment.

FIG. 17 is a flowchart illustrating the first analysis.

The first analysis is a series of processes of analyzing blood included in the test medium 110 by the blood testing apparatus 100. Referring to FIG. 17, the blood testing apparatus 100 acquires raw data of blood components from the blood included in the test medium 110 (operation 511).

The raw data is results of analysis executed by extracting respective components from the blood included in the test medium 110 without any correction. That is, the raw data includes kinds and concentrations (analysis results) of the respective blood components which are purely acquired by executing a predetermined test.

The blood testing apparatus 100 corrects the raw data based on setting information (operation 512).

The setting information includes factors which may influence the analysis results according to setting of the blood testing apparatus 100, such as an inner temperature of the blood testing apparatus 100 at the time of analysis, setting information of the test medium 110, and other setting information. The raw data may include an error according to the state of the blood testing apparatus 100 at the time of analysis. In the first analysis, in order to reduce such an error, the raw data is corrected based on the setting information.

The blood testing apparatus 100 acquires first correction values based on the setting information and stores the first correction values in the storage device 60 (operation 513).

That is, the first correction values are analysis results acquired by primarily correcting the raw data based on the setting information.

The blood testing apparatus 100 corrects the first correction values based on information about the input species of the animal (operation 514).

The blood testing apparatus 100 corrects the first correction values based on the species of the animal included in input information received from the user. In more detail, components of blood and ranges of concentrations of the respective blood components, which may be determined as normal ranges, are varied according to animal species. Therefore, the blood testing apparatus 100 acquires second correction values by adjusting the first correction values once again based on the species of the animal included in the received input information (operation 515).

When the second correction values are acquired based on the species of the animal, the blood testing apparatus 100 outputs the second correction values as analysis results (operation 516).

When the input information input by the user is incorrect, the related art blood testing apparatus executes the above-described first analysis all over again and thus has low efficiency in testing. However, the blood testing apparatus 100 according to an embodiment induces the user to change the input information and executes only a second analysis based on a newly input species of the animal, thus improving efficiency in testing.

Figure 18:
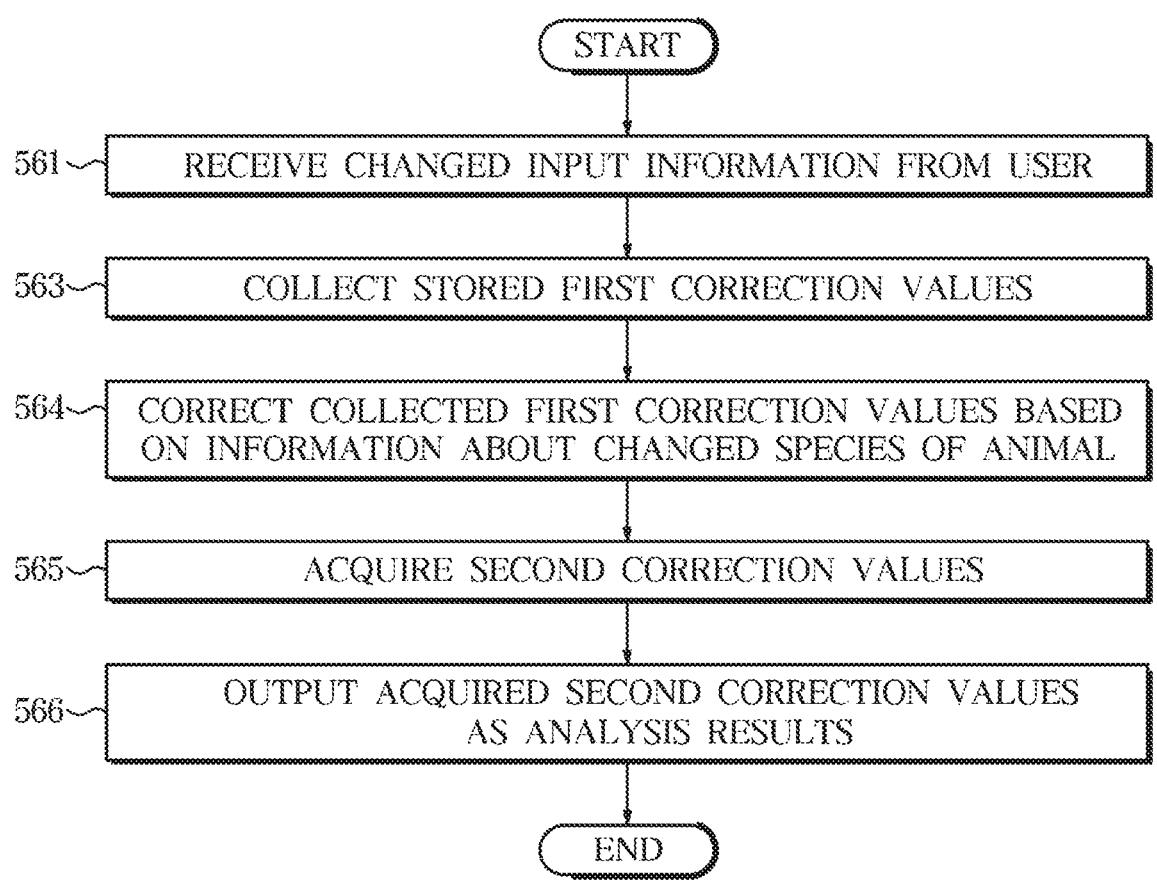
FIGS. 18 and 19 are flowcharts illustrating an analysis according to an embodiment.
Figure 19:
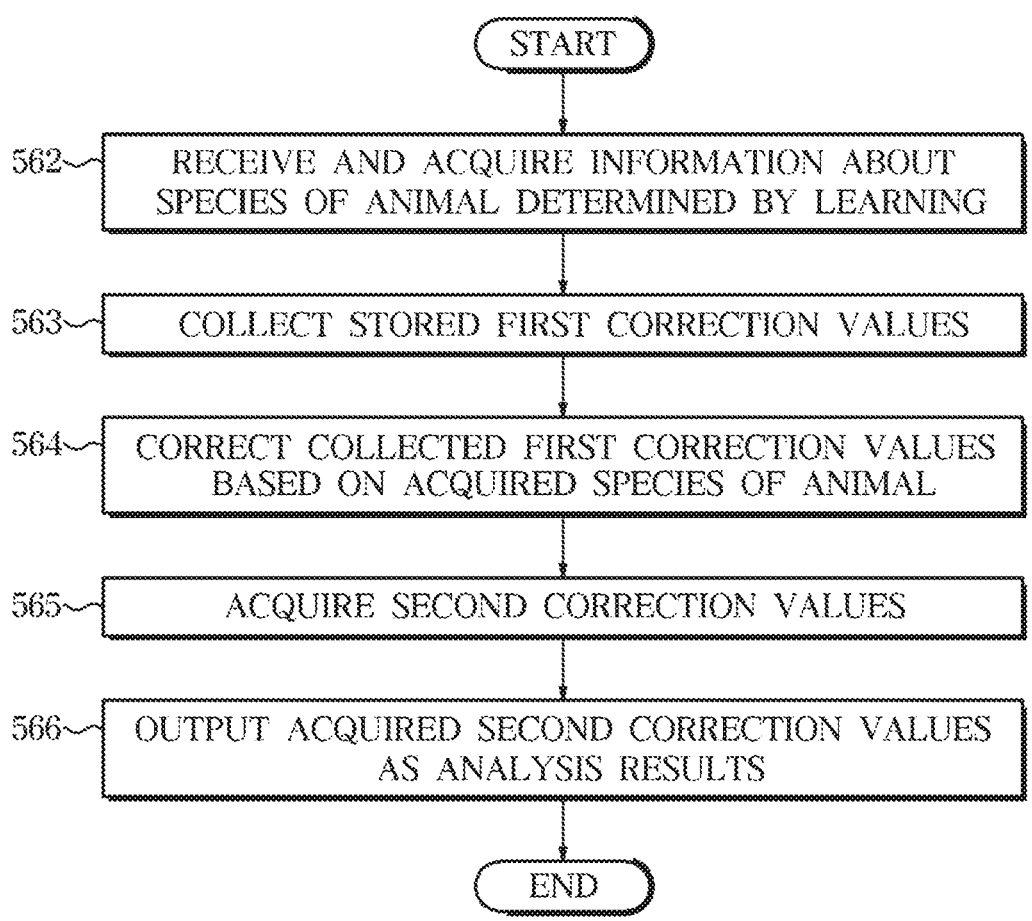

FIGS. 18 and 19 are flowcharts illustrating embodiments included in the second analysis.

Referring to FIG. 18, the blood testing apparatus 100 receives changed input information from the user (operation 561).

The blood testing apparatus 100 collects the stored first correction values of the blood components (operation 563).

As described above with reference to FIG. 17, the first correction values are analysis results acquired by correcting the raw data acquired in the first analysis based on the setting information. The first correction values may be stored in the storage device 60 and loaded when the second analysis is executed.

The blood testing apparatus 100 corrects the collected first correction values based on the changed species of the animal included in the change input information (operation 564).

As described above with reference to FIG. 17, in the first analysis, the first correction values are also executed based on the input species of the animal. When a changed species of the animal is input after the first correction values are stored, the blood testing apparatus 100 according to an embodiment does not newly execute analysis, but executes only correction of the first correction values based on the changed species of the animal, thus shortening a testing time.

For example, a time taken to correct the first correction values is about 10 seconds to 30 seconds, as exemplarily shown by a graphics in interface 2010 of in FIG. 20B and, thus, a testing time may be shortened, as compared to about 5 minutes which is necessary to execute the first analysis.

The blood testing apparatus 100 acquires second correction values (operation 565).

The blood testing apparatus 100 outputs the acquired second correction values as analysis results through the display 40 (operation 566).

Referring to FIG. 19, a blood testing apparatus 100 according to an embodiment may acquire information about a species of the animal determined through learning (operation 562), collect stored first correction values (operation 563), and correct the first correction values based on the acquired species of the animal (operation 564).

The blood testing apparatus 100 according to an embodiment may execute the second analysis based on the determined animal species, when the input species of the animal does not coincide with the species of the animal determined through learning. That is, the blood testing apparatus 100 may correct the first correction values based on the determined species of the animal without output of an interface configured to induce the user to change input information.

Thereby, the blood testing apparatus 100 may omit change of the input information by the user and save a time taken to execute a retest due to incorrect input.

As apparent from the above description, a blood testing apparatus and a control method thereof according to an embodiment may predict a species of an animal using test results and, when a species of the animal chosen by a user prior to a test is different from the predicted species of the animal, e.g., analyzed species of the animal, give a warning to the user through various interfaces, thereby preventing misdiagnosis due to incorrect choice of a species of the animal.

Although a few embodiments have been shown and described, it would be appreciated by those skilled in the art that changes may be made in the embodiments without departing from the principles and spirit of the disclosure, the scope of which is defined in the claims and their equivalents.

What is claimed is:

1. A blood testing apparatus comprising:
    an input device configured to receive an input information identifying an animal from a user;
    an analyzer configured to analyze blood components of an animal based on the input information, the blood components being included in a test medium;
    an output device configured to display analysis results of the blood components; and
    a controller configured to determine a species of the animal based on at least one from among types of the blood components and the analysis results of the blood components and control the output device to display a visual indication representing the determined species of the animal as determined by the controller,
    wherein the controller is further configured to compare the determined species of the animal with a species of the animal included in the input information input by the user, and output an interface configured to prompt the user to change the input information of the species of the animal, based on a comparison result,
    wherein the controller is further configured to determine the species of the animal based on a learning model obtained through machine learning using a neural network for the types of the blood components and the analysis results of the blood components.

2. The blood testing apparatus according to claim 1, wherein the controller is further configured to confirm the species of the animal whose blood components are in the test medium, compare the confirmed species of the animal with the species of the animal included in the input information, and control the analyzer based on a comparison result.

3. The blood testing apparatus according to claim 2, wherein the controller is further configured to confirm the species of the animal through at least one from among a barcode, a Quick Response (QR) code, an radio frequency identification (RFID) tag, and a Universal Serial Bus (USB) chip included in the test medium.

4. The blood testing apparatus according to claim 2, wherein the controller is further configured to control the output device to display an interface configured to prompt the user to change the input information of the species of the animal, based on the comparison result of the confirmed species of animal and the species of the animal included in the input information.

5. The blood testing apparatus according to claim 1, further comprising a local memory, wherein the controller is further configured to extract raw data of the blood components through the analyzer, execute a first analysis based on the raw data and determine the species of the animal based on analysis results of the first analysis, wherein the first analysis comprises a decision tree of the learning model stored in the local memory, and the controller determines the species of the animal based on the first analysis.

6. A blood testing apparatus comprising:
    an input device configured to receive an input information identifying an animal from a user;
    an analyzer configured to analyze blood components of an animal based on the input information, the blood components being included in a test medium;
    an output device configured to display analysis results of the blood components; and
    a controller configured to determine a species of the animal based on at least one from among types of the blood components and the analysis results of the blood components and control the output device to display a visual indication representing the determined species of the animal as determined by the controller,
    wherein the controller is further configured to compare the determined species of the animal with a species of the animal included in the input information input by the user, and output an interface configured to prompt the user to change the input information of the species of the animal, based on a comparison result,
    wherein the controller determines the species of the animal through reiterative clustering analysis results which are not based on predetermined reference values.

7. The blood testing apparatus according to claim 1, wherein the controller is further configured to update the learning model by calculating first output values of activation functions based on weights set according to the types of the blood components and the analysis results of the blood components, and by varying the weights based on differences between the first output values and the species of the animal included in the input information.

8. A control method of a blood testing apparatus, the control method comprising:
    receiving an input information identifying an animal from a user;
    analyzing blood components of an animal based on the input information, the blood components being included in a test medium;
    determining a species of the animal based on at least one from among types of the blood components and analysis results of the blood components; and
    displaying the analysis results of the blood components and a visual indication representing the determined species of the animal, wherein the determined species is determined by a processor,
    wherein the control method further comprises:
    comparing the determined species of the animal with a species of the animal included in the input information input by the user, and
    outputting an interface configured to prompt the user to change the input information of the species of the animal, based on a comparison result,
    wherein the determining the species of the animal comprises:
    extracting raw data of the blood components;
    executing a first analysis based on the species of the animal included in the input information; and
    determining the species of the animal based on analysis results of the first analysis, wherein the first analysis is performed by a controller and comprises at least one of 1) a decision tree of learning models using plural blood components and 2) reiterative clustering analysis results which are not based on predetermined reference values.

9. The control method according to claim 8, further comprising:
   confirming a species of the animal whose blood components are in the test medium prior to the analyzing the blood components; and
   displaying a result of a comparison between the confirmed species of the animal and the species of the animal included in the input information.

10. The control method according to claim 8, wherein the blood components analyzed include at least one of albumin, glucose, alkaline phosphatase, alanine amino transferase, aspartate amino transferase, creatine, and gamma gutamyl peptidase.

11. The control method according to claim 8, wherein the determining the species of the animal comprises:
   determining the species of the animal based on whether the analysis results of the blood components are predetermined reference values or more.

12. The control method according to claim 8, wherein the test medium is a first test medium, and the determining the species of the animal comprises:
   determining the species of the animal based on the blood components extracted from the first test medium and the blood components extracted from a second test medium, the blood components extracted from the second test medium having the types which are different from those of the blood components extracted from the first test medium.

13. A non-transitory computer-readable recording medium storing instructions thereon, which when executed by a processor of a computer system, cause the processor to execute the method of claim 8.

* * * * *